(12) United States Patent
Jaffe et al.

(10) Patent No.: US 7,748,280 B2
(45) Date of Patent: Jul. 6, 2010

(54) SIDESTREAM GAS SAMPLING SYSTEM WITH CLOSED SAMPLE CIRCUIT

(75) Inventors: Michael B. Jaffe, Cheshire, CT (US); David R. Rich, Glastonbury, CT (US)

(73) Assignee: Ric Investments, LLC, Wilmington, DE (US)

( * ) Notice: Subject to any disclaimer, the term of this patent is extended or adjusted under 35 U.S.C. 154(b) by 20 days.

(21) Appl. No.: 11/771,268

(22) Filed: Jun. 29, 2007

(65) Prior Publication Data

US 2008/0041172 A1  Feb. 21, 2008

Related U.S. Application Data

(60) Provisional application No. 60/818,769, filed on Jul. 6, 2006.

(51) Int. Cl.
  *G01N 1/14* (2006.01)
(52) U.S. Cl. .................................................. 73/863.83
(58) Field of Classification Search .............. 73/863.83, 73/23.2
  See application file for complete search history.

(56) References Cited

U.S. PATENT DOCUMENTS

| | | | | | |
|---|---|---|---|---|---|
| 4,221,567 | A | * | 9/1980 | Clark et al. | 436/68 |
| 4,365,505 | A | * | 12/1982 | Holzl | 73/19.1 |
| 4,475,405 | A | | 10/1984 | Corporn et al. | |
| 4,706,502 | A | | 11/1987 | Jones et al. | |
| 4,764,344 | A | * | 8/1988 | Knab | 422/89 |
| 4,977,776 | A | * | 12/1990 | Shindo et al. | 73/1.03 |
| 5,090,256 | A | * | 2/1992 | Issenmann | 73/863.23 |
| 5,187,972 | A | * | 2/1993 | DeFriez | 73/23.2 |
| 5,205,177 | A | * | 4/1993 | DuBrock et al. | 73/863.12 |
| 5,235,843 | A | * | 8/1993 | Langhorst | 73/19.02 |
| 5,743,259 | A | * | 4/1998 | Kruse et al. | 600/309 |
| 5,861,316 | A | * | 1/1999 | Cage et al. | 436/52 |
| 5,957,839 | A | * | 9/1999 | Kruse et al. | 600/309 |
| 6,325,978 | B1 | | 12/2001 | Labuda et al. | |
| 6,632,402 | B2 | * | 10/2003 | Blazewicz et al. | 422/84 |
| 6,683,679 | B2 | | 1/2004 | Belenkii | |
| 2002/0098120 | A1 | * | 7/2002 | Blazewicz et al. | 422/82.07 |
| 2003/0190262 | A1 | * | 10/2003 | Blazewicz et al. | 422/94 |
| 2003/0191405 | A1 | | 10/2003 | Rich et al. | |
| 2004/0065141 | A1 | | 4/2004 | Rich | |
| 2004/0068224 | A1 | | 4/2004 | Couvillon, Jr. et al. | |
| 2006/0086254 | A1 | | 4/2006 | Fudge et al. | |
| 2006/0106345 | A1 | * | 5/2006 | Flaker et al. | 604/131 |
| 2007/0191789 | A1 | * | 8/2007 | Hickle | 604/257 |

OTHER PUBLICATIONS

U.S. Appl. No. 60/808,312, filed May 25, 2006, Russell.
U.S. Appl. No. 11/805,074, filed May 22, 2007, Russell.

(Continued)

*Primary Examiner*—John Fitzgerald (57) ABSTRACT

The invention provides a sidestream gas sampling apparatus having a gas sampling circuit and a set of reusable elements. The gas sampling circuit carries the gas sample from a main flow of gas, through a sample analysis area, and vents the gas sample to an analyzed gas destination. The reusable components provide motive forces to remove the gas sample through the gas sampling circuit and provide analysis components for the gas sampling apparatus while not making contact with the gas sample. As such, the reusable components do not become contaminated by the gas sample and do not have to be cleaned or sterilized between applications.

35 Claims, 6 Drawing Sheets

OTHER PUBLICATIONS

Weingarten, "Respiratory monitoring of carbon dioxide and oxygen: a ten-year perspective", J. Clin. Monit., Jul. 1990 6(3):217-25.

Tohyama et al., "A Fiber-Optic Pressure Microsensor for Biomedical Applications," 1997 International Conference on Solid-State Sensors and Actuators (Transducers '97), 1489-1492.

Ebelhack, "Peristaltic Pumps—Not Just for Labs Anymore, New Designs Offer Higher Flowrates and Pressure Capacities," originally published in Chemical Processing Magazine, Nov. 2000.

Ashley, "Artificial Muscles", Scientific American, Oct. 2003, p. 53-59.

* cited by examiner

SIDESTREAM GAS SAMPLING SYSTEM WITH CLOSED SAMPLE CIRCUIT

CROSS-REFERENCE TO RELATED APPLICATIONS

This application claims priority under 35 U.S.C. §119(e) from provisional U.S. patent application Ser. No. 60/818,769, filed Jul. 6, 2006, the contents of which are incorporated herein by reference.

BACKGROUND OF THE INVENTION

1. Field of the Invention

The invention relates to a sidestream gas sampling system having a gas sampling circuit that is closed to motive components and/or analysis components of the gas sampling system.

2. Description of the Related Art

Gas analysis apparatus are useful for many applications, including medical uses. Examples of medical uses of gas analysis apparatus include capnography and oxygraphy (or oxigraphy). Capnography refers to the measurement of carbon dioxide ($CO_2$) in a patient's breath. Oxygraphy refers to the measurement of oxygen ($O_2$) in patient's breath. These measurements may provide useful information regarding the patient's health. Additionally, other gases in the breath may be monitored for medical purposes including therapeutic gases (such as nitric oxide), anesthetic agents (such halothane) and trace gases used for diagnostic purposes (such as nitric oxide and carbon monoxide, which are typically present in the parts per million (ppm) or parts per billion (ppb) levels). Trace substances in the breath may reflect the concentration of the substance in the blood of the patient.

Information provided by capnography is used, for example, to detect incidents that may occur during medical procedures, particularly the detection of general anesthesia incidents. Additionally, information provided by capnography is used during clinical events such as, for example, cardiac or respiratory arrest. In fact, capnography can provide information in real-time regarding the effectiveness of resuscitative efforts during cardiac arrest. As such, capnography has multiple medical uses during medical procedures, during prolonged monitoring of patient vital signs, during clinical events, and other medical uses.

Oxigraphy also has multiple medical uses. Oxygraphy measures the approximate concentration of oxygen in the vital organs on a breath-by-breath basis and can quickly detect imminent hypoxemia due to decreasing alveolar oxygen concentration. For example, during hypoventilation, end tidal oxygen concentration changes more rapidly than does end tidal carbon dioxide. During the same conditions, pulse oximetry takes considerably longer to respond.

Oxygraphy has also been shown to be effective in diagnosing hypoglycemic or septic shock, air embolism, hyperthermia, excessive PEEP, CPPR efficacy, and even cardiac arrest. During anesthesia, oxygraphy is useful in providing a routine monitor of preoxygenation (denitrogenation). It especially contributes to patient safety by detecting human errors, equipment failures, and disconnections. A paper by M. Weingarten entitled "Respiratory monitoring of carbon dioxide and oxygen: a ten-year perspective" (J. Clin. Monit. Jul. 6, 1990(3):217-25), which is hereby incorporated by reference herein in its entirety, highlights some of the applications of monitoring carbon dioxide and oxygen in the patient's breath.

There are typically two principal methods of sampling gas for gas analysis. The first is mainstream gas analysis (i.e., non-diverting gas analysis), which measures the concentration of a gas or gases (e.g., a patient's breath) at a sample site located within the respiratory gas stream. For example, a patient being treated with a respirator has a patient circuit extending from his or her oral cavity that communicates a flow of gas between the respirator and the patient. A mainstream gas analyzer measures the concentration of a gas or gases within the patient circuit.

The other principal method of sampling gas for gas analysis is sidestream gas analysis (i.e., diverting gas analysis). Sidestream gas analysis transports gas away from the sample site and measures the concentration of gas or gases in the transported sample at a remote location. For example, if a patient is being treated by a respirator, a diverter/adaptor is coupled to the patient circuit to remove a portion of the gas traveling through the patient circuit and transport that gas a certain distance away from the patient to a gas measurement device. The concentration of the gas or gases within the sample may then be measured by the gas measurement device and the gas sample may then be disposed of.

The nature of sidestream gas analyzers imposes certain requirements as to their component parts. Similar to mainstream gas analyzers, sidestream gas analyzers must include analysis components (e.g., spectroscopic) and a sample chamber. Gas is transported into the sample chamber and the gas concentration is measured using the analysis equipment. In many instances, spectroscopic analysis equipment is employed, which uses the infrared absorption of gases of interest to measure the concentration of these gases in the sample (e.g., $CO_2$, $O_2$, anesthetic agents, etc.).

Sidestream gas analyzers may also include an apparatus such as, for example, a pump to create negative pressure that draws the gas sample from the sample site. Additionally, sidestream gas analyzers may include pressure measurement devices to measure the pressure within the sampling apparatus. Information regarding the pressure within the sampling apparatus may be useful to measure and/or correct for the effects that pressure within the sampling apparatus has on the absorption of infrared radiation by gases in the sample. Pressure measurements may also be useful for recording and/or compensating for pressure drops or other fluctuations within the sampling tubing and other components of the sampling apparatus. Other uses for pressure measurements may also exist.

Furthermore, sidestream gas analyzers may include flow measurement devices to measure the flow of gas through the sampling apparatus. Information regarding the flow within the sampling apparatus may be used to adjust or regulate the pump to maintain a constant flow rate within the sampling apparatus under a variety of load conditions. A constant flow rate may be desirable when measuring gas concentration over an extended period of time, as it simplifies the compensations required. Less constant flow within a sampling apparatus may also be used, but requires additional compensation calculations. Flow rate information may also be useful for other purposes.

In some environments, the sampled gas may be routed back into the patient circuit after analysis by a sidestream gas analyzer. This is sometimes done, for example, in situations where an expensive anesthetic is used on the patient that can be conserved by reintroducing it into the patient circuit. Additionally, the sampled gas of the patient often contains contaminants (e.g., mucus, blood, medications, or other materials). Routing these materials back into the patient circuit is sometimes considered a viable option for placement of an analyzed sample containing these contaminants.

However, when routing analyzed gas back into a patient circuit using a typical sidestream gas analyzer, care should be taken to prevent contamination of the internal capnometer parts. In a typical sidestream gas analyzer, sampled gas makes contact with pump parts, pressure measurement parts, flow measurement parts, tubing, water traps, and/or other parts of the capnometer. If the sidestream gas analyzer is to be used on multiple patients, the patients may be at risk from cross-contamination if the sampled gas is routed back into the patient circuit via a connection to an exhaust port or purging of the sampling lines to keep them clear. Because many of these parts are relatively complex (e.g., pumps, pressure transducers, flowmeters, spectroscopic equipment, or other complex parts), the cost of replacing them due to degradation in performance or occlusion from excessive exposure to contaminants may be large.

SUMMARY OF THE INVENTION

Accordingly, it is an object of the present invention to provide a sidestream gas sampling apparatus that overcomes the shortcomings of conventional sidestream gas sampling apparatus. This object is achieved according to one embodiment of the present invention by providing a sidestream gas sampling apparatus having a gas sampling circuit that contacts the gas sample and having certain components that do not make contact with a gas sample in the gas sampling circuit. This configuration prevents contamination of the gas non-contacting components by contaminants that may be in the gas sample, thereby minimizing the potential for cross-contamination, occlusion, and performance degradation of these components between applications. This configuration may reduce the manufacturing, operating, and/or maintenance costs of the sidestream gas sampling apparatus because the gas-contacting components are easily replaced while the gas non-contacting components are reused in subsequent measurements.

It is a further object of the present invention to provide a method for measuring a concentration of one or more components of a gas sample taken from a mainstream flow of gas that overcomes shortcomings of conventional sidestream gas sampling methods. This object is achieved according to one embodiment of the present invention by providing a method that includes removing a gas sample from a mainstream flow of gas, transporting the gas sample to a sample analyzer region via a sample transport tube, measuring a characteristic of the one or more components within the gas sample in the sample analyzer region.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

One aspect of the invention provides a sidestream gas sampling apparatus having a gas sampling circuit that contacts the gas sample and a set of reusable components that do not make contact with a gas sample in the gas sampling circuit. This configuration prevents contamination of the reusable components by contaminants in the gas sample and prevents cross-contamination of the reusable components between patients or patient applications. This configuration may reduce the manufacturing, operating, and/or maintenance costs of the reusable components.

Figure 1A:
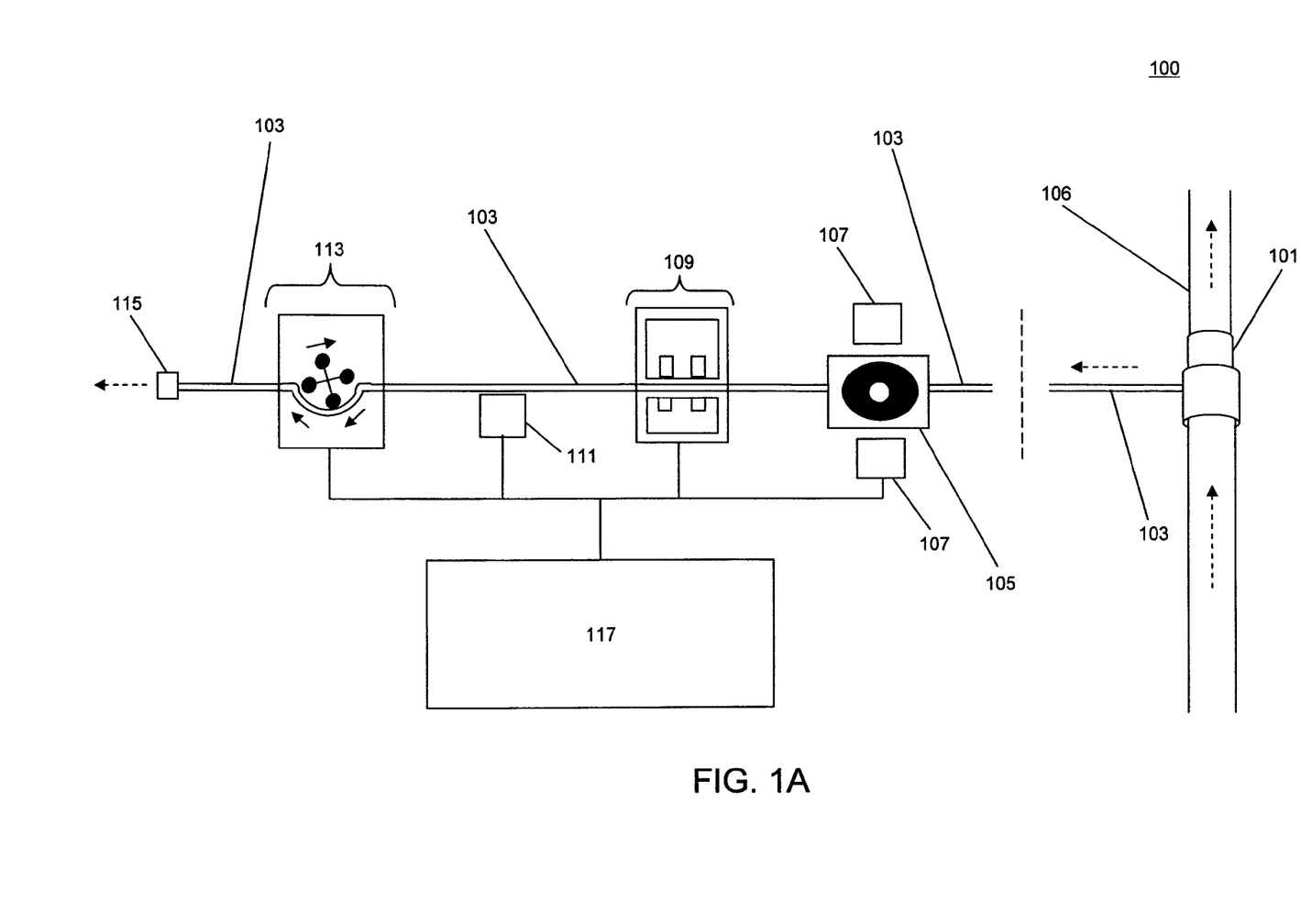
FIG. 1A is a schematic view of a gas sampling apparatus according to an embodiment of the invention.

FIG. 1A illustrates gas sampling apparatus 100 according to an exemplary embodiment of the invention. Gas sampling apparatus 100 includes an airway adaptor 101, a tubing set 103, a sample cell 105, measurement optics 107, a flow measurement device 109, a pressure measurement device 111, a pump 113, an exhaust port 115, a control center 117, and/or other elements.

Figure 1B:
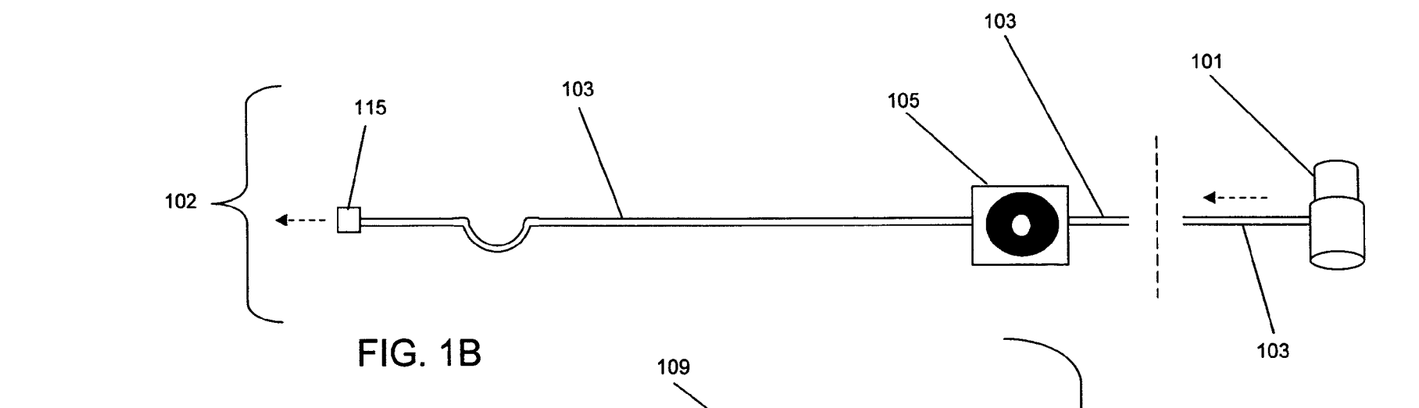
FIG. 1B is a schematic view of a gas sampling circuit in the gas sampling apparatus of FIG. 1.
Figure 1C:
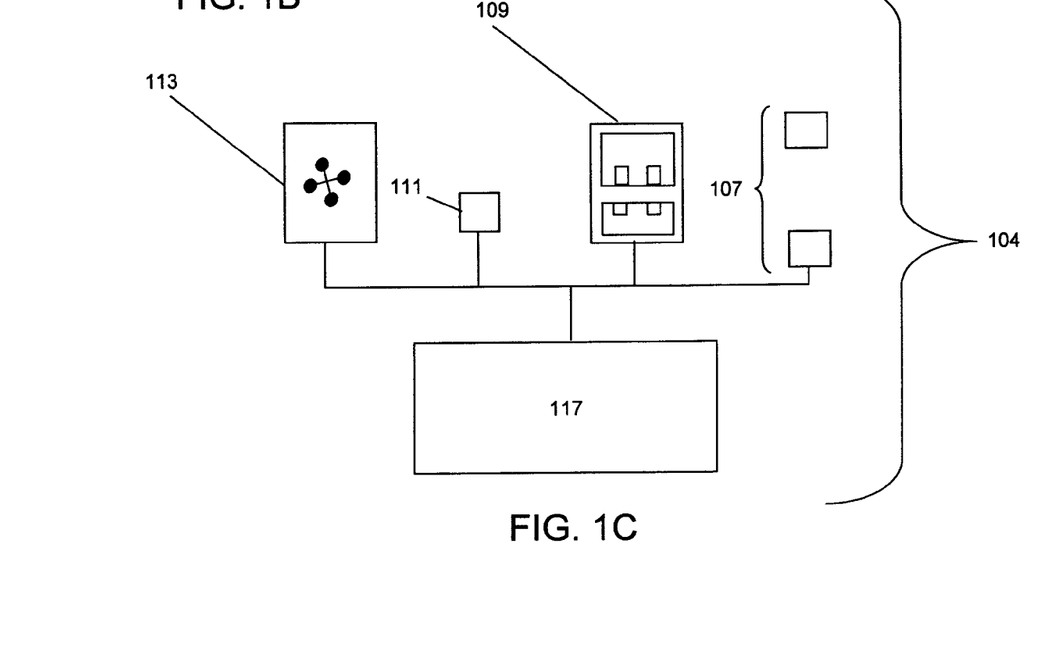
FIG. 1C is a schematic view of reusable components of the gas sampling apparatus of FIG. 1.

FIG. 1B illustrates a gas sampling circuit 102 and FIG. 1C illustrates reusable components 104 used in gas sampling apparatus 100. Gas sampling circuit 102 may include all of the components of gas sampling apparatus 100 that come into contact with the gas sample. For example, gas sampling circuit 102 may include airway adaptor 101, tubing set 103, sample cell 105, and exhaust port 115. Reusable components 104 may include those components of gas sampling apparatus that do not come into contact with the gas sample such as, for example, measurement optics 107, flow measurement device 109, pressure measurement device 111, pump 113, control center 117, and/or other components.

In some embodiments, gas sampling circuit 102 may be disposable, and thus may be manufactured such that the components of gas sampling circuit 102 are suitable for use with a single patient. As such, the relatively simple and/or inexpensive parts of gas sampling apparatus 100 that comprise gas sampling circuit 102 can be discarded between patients, while relatively complex and/or expensive components comprising reusable components 104 can be re-used with other patients without concerns of cross-contamination between applications.

In other embodiments, gas sampling circuit 102 need not be disposable, but may be easily and/or repeatedly cleaned or sterilized. This may reduce the complexity, manufacturing costs, and/or operating costs of gas sampling apparatus 100, as only the components comprising gas sampling circuit 102 need be manufactured for repeated sterilization or cleaning, while the components comprising reusable components 104 need not endure repeated sterilization or cleaning (e.g., they may be less expensive to manufacture, use, maintain, and/or may last longer).

In one embodiment, gas sampling apparatus may obtain a gas sample from a main flow of gas 106 via airway adaptor 101. In some embodiments, main flow of gas 106 may be the airway circuit of a respirator or other medical device in fluid communication with the respiratory system of a patient. In these embodiments, airway adaptor 101 may comprise a "T" junction, "Y" junction, or other interface to main flow of gas 106.

In other embodiments, airway adaptor 101 may interface with the respiratory system of the patient and may be replaced with a face mask, nasal cannula, nasal adaptor, intubation equipment or adaptor thereto, or other interfaces. Other adaptors enabling withdraw of gas samples from the aforementioned or other gas flows may be used.

Tubing set 103 may include one or more lengths of sample transport tubing or other conduit that enables transport of a gas sample from airway adaptor 101 to sample cell 105 and/or between other components of gas sampling apparatus 100. For example, tubing set 103 may include medical-grade plastic tubing compliant for use in sidestream capnography.

Sample cell 105 and measurement optics 107 enable measurement of one or more characteristics of one or more specific components within the gas sample. In one embodiment, measurement of one or more characteristics of a component includes measuring the concentration of the component within the gas sample, partial pressure of the component within the gas sample, presence or absence of the component in the gas sample, and/or other characteristics. For example, sample cell 105 and measurement optics enable the measurement of the concentration of carbon dioxide ($CO_2$) in the gas sample. The concentration or other characteristics of other components such as, for example, oxygen ($O_2$), carbon monoxide (CO), nitric oxide (NO), anesthetic agents (e.g., halothane), contaminants, trace gasses, particulates, or other substance within the gas sample may also be measured. In one embodiment, if the measured characteristic of a component within the gas sample is concentration, the measurement may be measured, expressed, or reported as a percentage of the gas sample, parts per million (ppm) in the gas sample, parts per billion (ppb) in the gas sample, or other units of measurement.

To measure a characteristic of the one or more specified components in the gas sample, the gas sample may be passed through sample cell 105, wherein measurement optics 107 measure the characteristic of the one or more specified components in the gas sample. As such, sample cell 105 may include an inlet for enabling the gas sample to pass into a sample analyzer/analysis region of sample cell 105. As mentioned herein, the gas sample may include a continuous stream of gas and discrete measurements of the characteristic of the one or more specified components in the stream of gas may be obtained over a period of time.

In one embodiment, gas sampling apparatus 100 includes a filter (not illustrated) between adapter 101 and sample cell 105 to remove contaminants or other unwanted materials from the gas sample. In one embodiment, the filter may be integrated into a portion of tubing set 103 between airway adaptor 101 and sample cell 105. In one embodiment, the filter may be incorporated into sample cell 105 such that the gas sample passes through the filter prior to entering the sample analysis region of sample cell 105. Other configurations incorporating one or more filters in other portions of gas sampling apparatus 100 may also be used.

Example of a filters, sample cells, and filter/sample cell combinations suitable for use in the present invention is disclosed in U.S. patent application Ser. No. 10/678,692 (publication no. US-2004-0065141), U.S. patent application Ser. No. 11/266,864 (publication no. US-2006-0086254), and U.S. patent application Ser. No. 10/384,329 (publication no. US-2003-0191405) ("the '329 application") the contents of each of which are incorporated herein by reference.

The analysis region of sample cell 105 may include two windows. A first window enables electromagnetic radiation from measurement optics 107 to pass into the analysis region. A second window enables the electromagnetic radiation to pass out of the analysis region after passing through the gas sample.

In one embodiment, measurement optics 107 comprise at least a source assembly and a detector assembly. In one embodiment, the one or more specified components whose characteristics are measured comprises $CO_2$. As mentioned above, the characteristics of other components may be measured. In one embodiment, infrared radiation is used to measure the characteristics of components in the gas sample. In this embodiment, the detector assembly may include an infrared detector and the source assembly may include an infrared emitter.

Figure 2A:
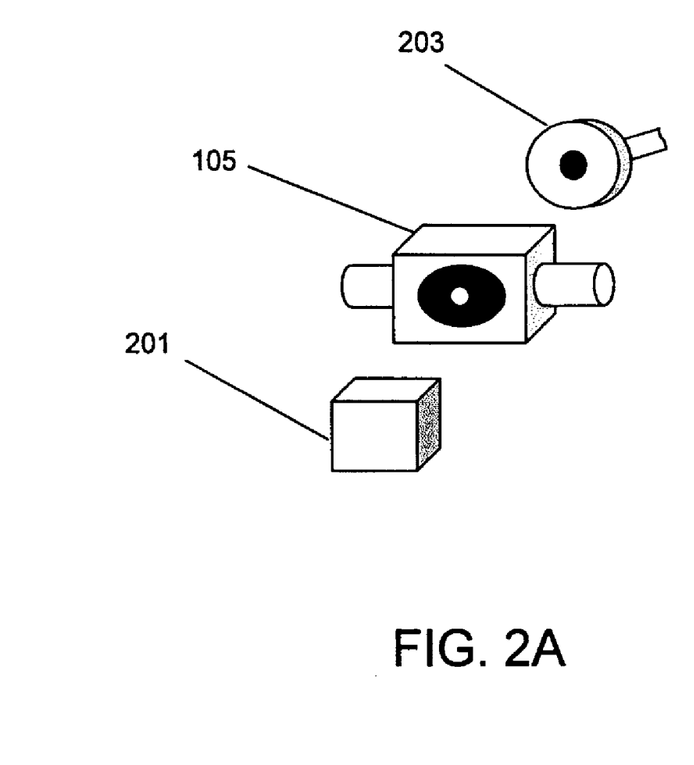
FIGS. 2A and 2B are more detailed illustrations of a sample cell and measurement optics according to an embodiment of the invention.
Figure 2B:
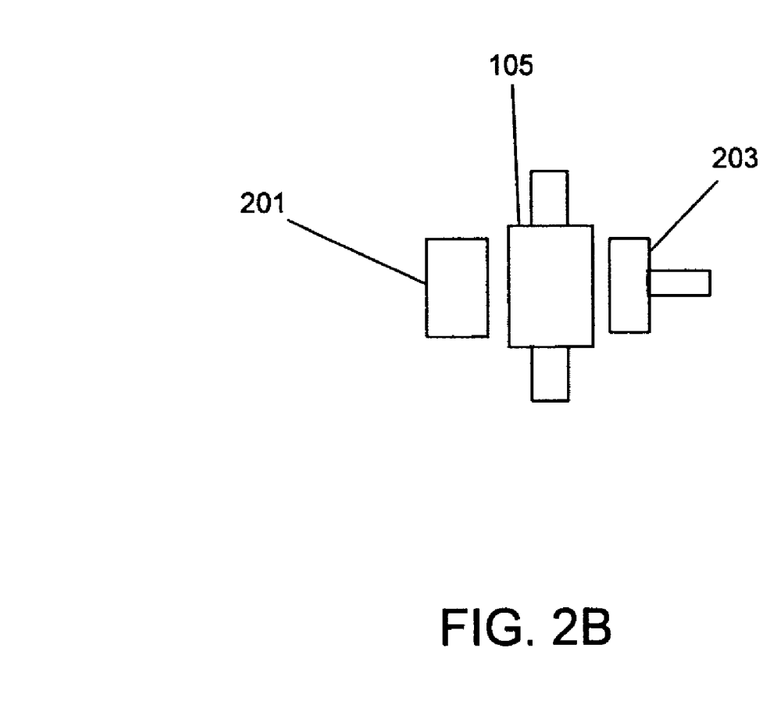

FIGS. 2A and 2B are more particular illustrations of an embodiment of the invention wherein sample cell 105 is placed between a source assembly 201 and a detector assembly 203 of measurement optics 107. As mentioned above, in some embodiments, source assembly 201 may emit infrared radiation (IR) for the detection of specific components in the gas sample. The infrared radiation emitted by source assembly 201 may be pulsed or constant. If the infrared radiation is constant, a mechanical chopper (not illustrated) may be used. Detector assembly 203 may include a detector sensitive to infrared radiation such as, for example, a lead selenide detector.

Sample cell 105 may be positioned between source assembly 201 and detector assembly 203 such that infrared radiation emitted from source assembly 201 passes through the first window of sample cell 105 into the sample analysis region of sample cell 105. Each specific component present in the gas sample may then absorb infrared radiation of particular wavelengths from the emitted infrared radiation as it passes through the sample analysis region. The remaining infrared radiation then passes out of sample cell 105 through the second window. Detector assembly 203 detects the remaining infrared radiation. In one embodiment, the detector assembly 203 sends a signal to a processor or controller of control center 117, which then determines the wavelengths of the infrared radiation absorbed by the components within the gas sample. This information is used to determine the concentration of $CO_2$ and/or other component within the gas sample.

In one embodiment, sample cell 105 may include the sample cell utilized by the Respironics LoFlo™ C5 Sidestream System. Additional information regarding sample cells, measurement optics, and other elements that can be used with the systems and methods of the invention can be found in the '329 application.

In some embodiments, sample cell 105 need not be a separate component of gas sampling apparatus 100, but may comprise radiation inlet and outlet windows and/or a sample analysis region that are part of, or integrated into, a portion of tubing set 103.

As described herein, measurement optics 107 may measure the concentration or other characteristic of one or more components within the gas sample without making contact with the gas sample itself. As such, any contaminants within the gas sample do not contact measurement optics 107, such that measurement optics 107 are not contaminated by the gas sample. Therefore, the use of measurement optics 107 in subsequent capnography applications does not expose patients to contaminants from previous patients.

While the measurement portion of gas sampling apparatus 100 is illustrated as measurement optics 107 in the figures, other methods of measurement involving the use of other devices or apparatus may be employed in the invention. For example, in one embodiment, the measurement portion of gas sampling apparatus 100 may comprise a luminescence quenching apparatus. In these embodiments, the sample analysis region of the sample cell may include an aperture in which a window that facilitates the detection of luminescence quenching is placed.

Luminescence quenching is defined as the radiationless redistribution of excitation energy via interaction (electronic energy or charge transfer) between an emitting species and a quencher, and is a technique that has been used to measure the concentration of gases such as oxygen (or other gases). The window which often serves as the sensor comprises a polymeric membrane in which a luminescable composition such as a porphyrin dye is dispersed. The sensor membrane is the mediator that brings about a dye-gas interaction in a controlled fashion. In a functional sensor, the dye is dispersed in the polymeric membrane, and a gas such as oxygen diffuses through the polymer. In use of luminescence quenching to measure oxygen concentrations, a material is excited to luminescence. Upon exposure of the luminescing material to a gas mixture including oxygen, the luminescence is quenched, depending upon the amount (i.e., concentration or fraction) of oxygen to which the luminescable material is exposed, or the amount of oxygen in the gas mixture. Accordingly, the rate of decrease in the amount of luminescence, or quenching of luminescence, of the luminescable material (i.e., the amount of light emitted by the luminescable material) corresponds to the amount of oxygen in the gas mixture. Additional information regarding luminescence quenching can be found in U.S. Pat. No. 6,325,978, which is hereby incorporated by reference herein in its entirety.

Typically, luminescence quenching requires the emission of excitation radiation from a source toward a material coated with or containing a luminescence chemistry that may be quenched by, or is specific for, one or more types of gas (e.g., oxygen, carbon dioxide, halothane, etc.) to be measured. The excitation radiation causes the material to be excited and to emit electromagnetic radiation of a different wavelength than the excitation radiation. The presence of the one or more gases of interest quenches, or reduces the amount of radiation emitted from the luminescable material. The amount of radiation emitted from the luminescable material is measured by a detector and compared with the amount of radiation emitted from the luminescable material in the absence of one or more quenching gases in order to facilitate a determination of the amount of the one or more sensed, quenching gases in the respiration of a patient.

It is also contemplated that the sample cell may include electrical contacts permitting physical communication with solid state gas sensors such gas-sensitive solid state semiconductor sensors and surface acoustic wave (SAW) sensors. Coating the SAW devices with different polymeric materials (that selectively absorb different gases) allows gas detection by changes in SAW frequency. These devices can be manufactured rather cheaply and permit measurement of a range of gases and trace substances.

In one embodiment, gas sampling apparatus 100 may also include a flow measurement device 109. In some embodiments, flow measurement device 109 may include a device that measures the flow of gas within gas sampling circuit 102 (e.g., the volume of gas passing through gas sampling circuit 102 over time). The measurement of gas flow within gas sampling circuit 102 aids in maintaining a constant rate of gas flow through gas sampling circuit. For example, if the flow of gas through gas sampling circuit 102 becomes too high or too low, as detected by flow measurement device 109, pump 113 may be adjusted (e.g., sped up or slowed down) to correct for this fluctuation, thus maintaining a constant flow rate within gas sampling apparatus 100. A constant flow rate may be important to recording an accurate profile of a characteristic of a component in a patient's exhaled breath over time (it may be possible to correct for errors caused by an inconsistent flow rate if the variations in the flow rate are known).

In some embodiments, flow measurement device 109 may measure the flow of gas within gas sampling circuit 102 without coming into contact with the flow of gas. As stated above, this prevents contamination of flow measurement device 109 and enables to use of a gas sampling circuit that is completely closed from the reusable components 104 of gas sampling apparatus 100.

In one embodiment, flow measurement device 109 may include an optical flowmeter. For example, in one embodiment, an optical flowmeter may measure the flow of gas by correlating interference signals produced by coherent laser beams (or other electromagnetic energy) passing through the flow of gas within gas sampling circuit 102. The interference correlation optical flowmeter of this example includes at least two laser beams that are shot in a transverse manner across the flow of gas within gas sampling circuit 102 (e.g., across a region of tubing set 103). The region of tubing set 103 or other portion of gas sampling circuit 102 across which the laser beams are shot may include two or more optical windows that allow each of these laser beams to enter and exit gas sampling circuit 102 while passing transversely across the flow of gas. After each of the laser beams exits gas sampling circuit 102, it is detected by a detector associated with flow measurement device 109. As each of the laser beams pass through the flow of gas, they contact turbulence within the flow of gas. Contact with this turbulence produces interference fringes that can be detected by the detectors associated with flow measurement device 109. Analysis of these interference fringes can reveal when the same patch of turbulence passes each of the laser beam paths. The time it takes the same patch of turbulence to pass through the laser beam paths is measured and used, along with the known spacing of the laser beam paths, to determine the flow rate within gas sampling circuit 102.

Additional information regarding a laser-enabled optical flowmeter, such as the one described herein, can be found in U.S. Pat. No. 6,683,679, which is hereby incorporated by reference herein in its entirety. Information regarding optical flow measurement and other types of measurement that can be used with the systems and methods of the invention can be found in U.S. patent application No. 60/808,312 entitled "Airway Adaptor with Optical Pressure Transducer and Method of Manufacturing A Sensor Component," which is hereby incorporated by reference herein in its entirety. The preceding example of optical flow measurement is exemplary only. Other types of optical flow measurement can be used.

Another example of a flow measurement device 109 that does not make contact with the gas sample is a vortex shedding flowmeter. A vortex shedding flowmeter may include a sensing element that is disposed transversely across the flow of gas within gas sampling circuit 102 (e.g., a portion of tubing set 103). A sensing element may include, for example, a fiber optic element that enters gas sampling circuit 102 in a direction transverse to the flow of gas (e.g., orthogonal to a main axis of the section of tubing set 103 though which it passes), stretches transversely across the flow of gas itself, and exits gas sampling circuit 102 in a similar manner. The flow of gas within gas sampling circuit 102 past the sensing element causes the sensing element to oscillate as turbulent vortices are shed downstream from the sensing element. A detector associated with flow measurement device 109 detects the oscillations and the oscillation frequency of the sensing element. From the oscillation frequency, the flow rate within gas sampling circuit 102 can be calculated. Additional information regarding vortex shedding flowmeters can be found in U.S. Pat. Nos. 4,706,502 and 4,475,405, both of which are hereby incorporated by reference herein in their entirety. The description of a fiber-optic-enabled vortex shedding flowmeter is exemplary only. Other types of vortex shedding flowmeters may be used.

As mentioned above, use of a vortex shedding flowmeter may involve a sensing element that makes contact with the gas sample. Thus, the sensing element of the vortex shedding flowmeter may become contaminated by said contact. Nevertheless, the detector or other components of vortex shedding flowmeters need not come into contact with the gas sample in gas sampling circuit 102. In some embodiments, some or all of the detector or other components of the vortex shedding flowmeter may be separate from the sensing element used in flow detection such that the sensing element is essentially a part of gas sampling circuit 102 rather than part of flow measurement device 109.

In some embodiments, gas sampling circuit 102 may be manufactured with a sensing element incorporated therein. In other embodiments, sensing elements that are detachable from the vortex shedding flowmeter may be incorporated into gas sampling circuit 102 prior to use. The detector or other components of flow measurement device 109 may be connected to the disposable sensing element during use with a patient and may be detached and reattached to another sensing element of another gas sampling circuit 102 for use in subsequent applications. In such embodiments, flow measurement device 109 is not considered to contact the gas sample within gas sampling circuit, as the sensing element is not considered part of flow measurement device 109.

Other types of flow measurement devices may also be used. In some embodiments, flowmeters with one or more parts that make contact with the gas sample may be used. These types of flowmeters may include differential pressure flowmeters, variable area flowmeters, turbine flowmeters, vane flowmeters, impeller flowmeters, ultrasonic flowmeters, thermal mass flow sensors, and/or other types of flowmeters. In these embodiments, similar to the description of the vortex shedding flowmeter, the one or more parts that make contact with the gas sample may be detachable from the remaining parts of the flowmeter and/or may be easily cleaned or sterilized.

In one embodiment, gas sampling apparatus 100 may also include a pressure measurement device 111. Pressure measurement device 111 may measure the pressure (force over area) within gas sampling circuit 102. In some embodiments, pressure measurement information may be useful in calculating the concentration of one or more components in a gas sample. For example, the pressure of a gas on which spectroscopic analysis is performed may alter the measured signal at the detected absorption wavelengths during spectroscopic analysis. Other uses for pressure information within gas sampling apparatus 100 also exist.

In one embodiment, pressure measurement device 111 may measure the pressure in gas sampling circuit 102 without making contact with the gas sample. As mentioned above, this prevents contamination of pressure measurement device 111 and enables the use of a gas sampling circuit 102 that is completely closed from reusable components 104 of gas sampling apparatus 100.

An example of pressure measurement device 111 that does not make contact with the gas sample is a diaphragm-enabled pressure measurement device. A diaphragm-enabled pressure measurement device may include a detector that detects the deformation of a diaphragm, wherein the magnitude of the deformation of the diaphragm corresponds to the pressure within the system. For example, a portion of gas sampling circuit 102 may include a deformable diaphragm incorporated into, for example, the wall of a portion of tubing set 103 or the sample cell 105. As the pressure of the gas sample within gas sampling circuit 102 increases, the diaphragm expands. Pressure measurement device 111 may then detect the magnitude of the deformation/expansion of the diaphragm and correlate it to the pressure inside gas sampling circuit 102. Other types of pressure measurement devices that do not contact the gas sample may be utilized. Additional information regarding pressure measurement devices that can be used with the systems and methods of the invention can be found in O. Tohyama, M. Kohashi, M. Fukui & H. Itoh, "A Fiber-Optic Pressure Microsensor for Biomedical Applications," 1997 International Conference on Solid-State Sensors and Actuators (Transducers '97), 1489-1492, which is hereby incorporated by reference herein in its entirety.

In some embodiments, pressure measurement device 111 may include one or more parts that do come into contact with the gas sample (e.g., a pressure transducer having a sampling element disposed into tubing set 103). In these embodiments, the one or more parts that come into contact with the gas sample may be detachable from the remainder of the pressure measurement device such that they are considered part of gas sampling circuit 102 rather than part of pressure measurement device 111. In some embodiments these detachable parts may be disposable. In other embodiments, they may be easily cleaned or sterilized.

In one embodiment, gas sampling apparatus 100 may also include a pump 113. Pump 113 may include any device that transports fluids. For example, pump 113 may create negative pressure in gas sampling circuit 102 such that a gas sample is drawn from main flow of gas 106 (e.g., the tubing of a respirator, the respiratory system of a patient, or other flow of gas) and into gas sampling circuit 102 via airway adaptor 101. An example of pump 113 that includes a peristaltic pump is given below. However, in other embodiments, methods/apparatuses other than peristaltic or diaphragm pumps can be used to create negative pressure such as, for example, compressed air, a Venturi vacuum pump, an electroactive polymer activated pump, or other methods/apparatuses.

In some embodiments, pump 113 does not make contact with the gas sample in gas sampling circuit 102. As such, pump 113 is not contaminated by the gas sample and need not be cleaned or sterilized between patients or patient applications.

Figure 3A:
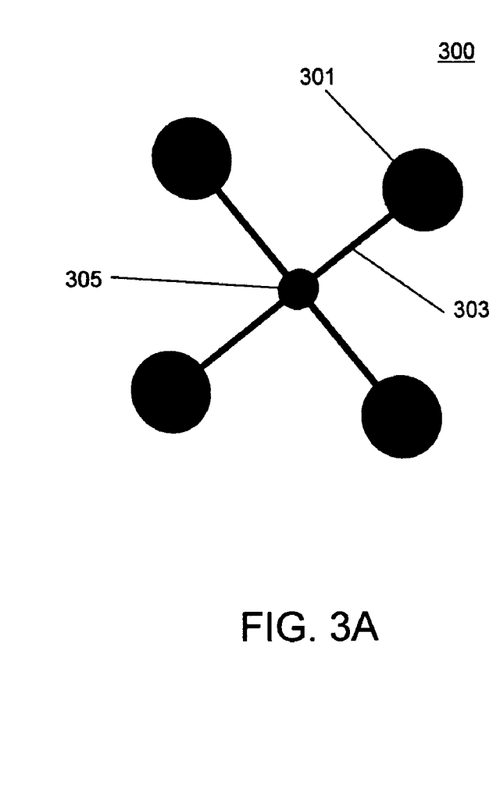
FIG. 3A is a schematic view of a roller system according to an embodiment of the invention.
Figure 3B:
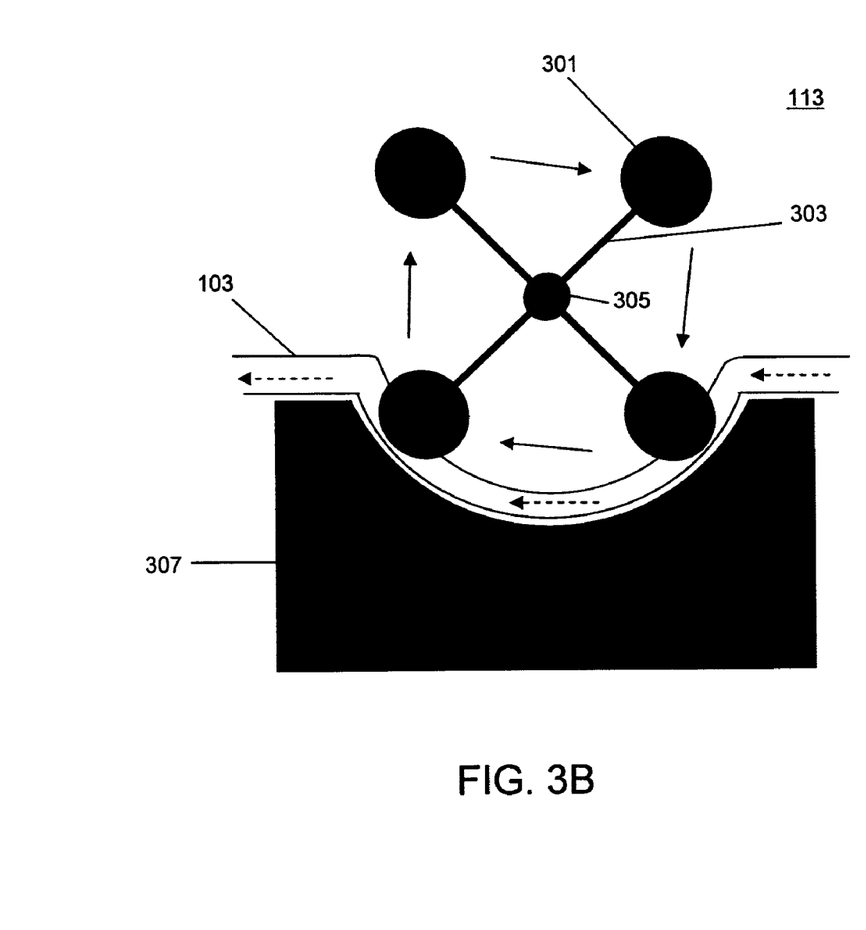
FIG. 3B is a schematic view of a peristaltic roller pump according to an embodiment of the invention.

In one embodiment, pump 113 may include a peristaltic roller pump. In one embodiment, a peristaltic roller pump as used in the invention may include a plurality of rollers set in a hub and spoke fashion. FIG. 3A illustrates a system 300 wherein a plurality of rollers 301 are set on the end of spokes 303, joined together at a hub 305. FIG. 3B illustrates pump 113 that incorporates roller system 300, a seat 307, and a portion of tubing set 103 from gas sampling circuit 102. The portion of tubing set 103 is laid into the seat 307, which, in this embodiment, includes a concave portion. Next, rollers 301 rotate around hub 305 (in this example, rollers rotate in a clockwise fashion). As a roller 301 comes into contact with tubing set 103, it compresses the wall of tubing set 301 and moves any fluid (e.g., gas) inside of the tubing in the direction in which roller 301 is traveling. The constant motion of the rollers 301 causes constant motion of the fluid in tubing set 103 in the direction in which the rollers 301 are traveling. This creates the negative pressure necessary to draw the gas sample from main flow of gas 106 through gas sampling circuit 102 of gas sampling apparatus 100. Additionally, no parts of pump 113 actually contact the gas sample. Therefore, pump 113 is not contaminated by the gas sample and requires no intervening sterilization between applications.

Additional information regarding peristaltic pumps can be found in Amy Ebelhack, "Peristaltic Pumps—Not Just for Labs Anymore, New Designs Offer Higher Flowrates and Pressure Capacities," originally published in Chemical Processing Magazine, November 2000, which is hereby incorporated by reference herein in its entirety. This document may also be found at http://www.coleparmer.com. The peristaltic roller pump illustrated in FIGS. 1, 3A, and 3B is exemplary only. Other types of pumps that do not make contact with the gas sample may also be used such as electroactive polymer actuated pumps with a removable chamber. Electroactive polymers are flexible materials that are capable of converting energy in the form of electric charge and voltage to mechanical force and movement. They provide unique opportunities to integrate functions that are segregated in traditional designs. The pump chamber may be contractile, thus permitting the integration of energy conversion, actuation, and structure into a single structure. An article by S. Ashley, titled "Artificial Muscles" (Scientific American, October 2003, p 53-59), which is hereby incorporated by reference herein in its entirety, highlights the capabilities of electroactive polymers. Additional information regarding electroactive polymer pumps can be found in U.S. patent application Ser. No. 10/384,329 (publication no. US 20040068224), entitled "Electroactive polymer actuated medication infusion pumps," which is hereby incorporated by reference herein in its entirety.

While FIGS. 1A and 1C illustrate pump 113 placed in a particular configuration in relation to the other elements of gas sampling apparatus 100, (i.e., downstream from sample cell 105, measurement optics 107, flow measurement device 109, and pressure measurement device 111), this placement is exemplary only. Pump 113 may be placed anywhere in relation to the other elements of gas sampling apparatus 100 necessary to transport fluid through gas sampling apparatus 100 as required by the invention.

In one embodiment, gas sampling apparatus 100 also includes an exhaust port 115. Exhaust port 115 may include a coupler or other device that joins tubing set 103 to a destination for the analyzed gas sample. In one embodiment, the destination for the analyzed gas sample may include the patient's breathing circuit. For example, the exhaust port may vent the analyzed gas sample back into the breathing circuit from which the gas sample was initially withdrawn. As mentioned above, this may be done for several reasons, including, to conserve expensive anesthetics or other drugs, to obviate the need for biohazard disposal, or for other reasons.

In one embodiment, the exhaust port 115 may vent the analyzed gas sample to a disposal system, wherein the gas is properly disposed of. In another embodiment, exhaust port 115 may vent the analyzed gas sample to a scavenging system wherein elements of the gas sample may be reclaimed prior to venting the gas to the atmosphere. Scavenging is the collection and removal of vented anesthetic gases from an operating environment. Because the amount of anesthetic gas supplied usually far exceeds the amount necessary for the patient, operating environment pollution is decreased by scavenging.

Scavenging may be active (suction applied) or passive (waste gases proceed passively down corrugated tubing through the exhaust grill of the OR). Active systems require a means to protect the patient's airway from the application of suction, or buildup of positive pressure. Passive systems require that the patient be protected from positive pressure buildup only. Another important distinction is that scavenger interfaces may be open (to the atmosphere) or closed (gases within the interface may communicate with the atmosphere only through valves; the more familiar type). The different types of interface have clinical implications. Open interfaces are found on all Julian™, Fabius GS™, Narkomed 6000™, and S/5 ADU™ gas machines. Aestiva™ machines may have an open or closed interface. Open interfaces may be safer for the patient.

A scavenger system may include a gas collection assembly, (e.g., tubes connected to APL and vent relief valve), transfer tubing (e.g., 19 or 30 mm, sometimes yellow color-coded), a scavenging interface, a gas disposal tubing (carries gas from interface to disposal assembly), a gas disposal assembly (active or passive—active most common, uses the hospital suction system), and/or other elements.

In some embodiments, exhaust port 115 may vent the analyzed gas sample to the atmosphere.

Figure 4:
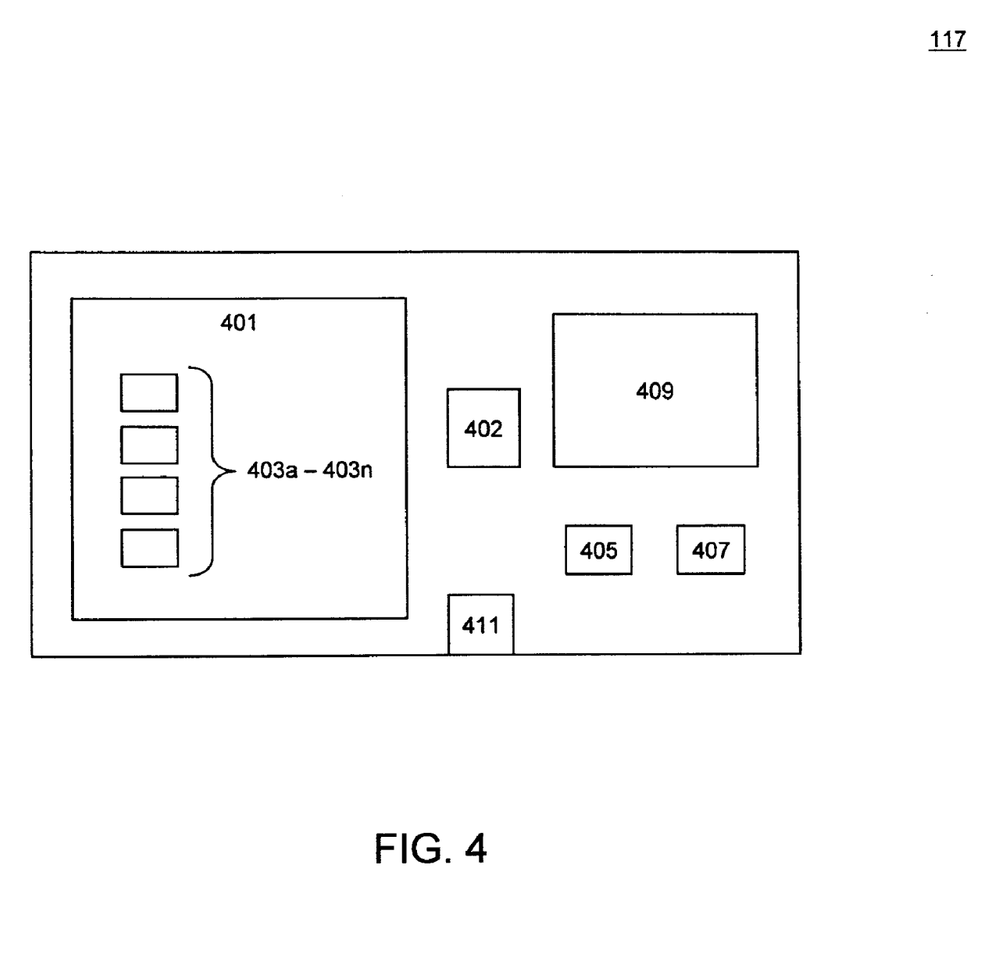
FIG. 4 is a schematic view of a control center according to an embodiment of the invention.

In one embodiment, gas analysis system 100 may also include a controller, processor, or "control center" 117 that electronically controls, regulates, monitors, and/or provides power to the components of gas sampling apparatus 100. FIG. 4 illustrates control center 117 according to an embodiment of the invention. In one embodiment, control center 117 includes a control application 401 run on a processor 402.

Control application 401 may comprise a software application residing on a memory of control center 117. In one embodiment, control application 401 may include one or more modules 403a-403n. Modules 403a-403n may include software modules enabling the control, regulation, monitoring, and or other tasks regarding gas sampling apparatus 100. Specifically, software modules 403a-403n may control the generation of infrared radiation by source assembly 201, enable measurement of the infrared radiation by detector assembly 203, enable the use of other measurement devices (luminescence quenching devices, solid state gas sensors, surface acoustic wave sensors, or other sensors or detectors), enable the measurement of one or more characteristics of one or more components in the gas sample (e.g., determine concentration of a component in the gas sample), regulate power to measurement optics 107, control any optics and/or electromagnetic energy generation necessary for flow measurement device 109 to measure flow of gas within gas sampling circuit 102, enable calculation of the flow of gas within gas sampling circuit 102, regulate power to flow measurement device 109, enable measurement of the deformation of a diaphragm for purposes of calculating the pressure within gas sampling circuit 102, enable calculation of the pressure within gas sampling circuit 102, regulate power to pressure measurement device 111, regulate operation of pump 113, regulate power to pump 113, enable the display of the contents of an analyzed gas sample and/or other information to a user via a graphical user interface, enable reception and calculations using input data from the user and/or other devices (e.g., medical devices), enabling output of data to other devices (e.g., display, printer, other medical equipment), and/or for performing other tasks related to gas analysis. One or more of modules 403a-403n comprising control application 401 may be combined. For some purposes, not all modules may be necessary.

In some embodiments, control center 117 may also include one or more input ports 405, for receiving input from a user (for example, via a keyboard or keypad), devices associated with gas sampling apparatus 100 (e.g., measurement optics 107, flow measurement device 109, pressure measurement device 111, pump 113, or other devices), and/or one or more other devices (e.g., other computing or medical devices). In some embodiments, control center 117 may also include one or more output ports 407 for providing output to one or more devices such as, for example, a display device, one or more devices associated with gas sampling apparatus 100 (e.g., measurement optics 107, flow measurement device 109, pressure measurement device 111, pump 113, or other devices), and/or other computing or medical devices. In some embodiments, control center 117 may include its own display device 409 for displaying data to a user via a graphical user interface.

In some embodiments, control center 117 may also include a power interface 411 for receiving power from direct current and/or alternating current power sources. In some embodiments, power received at power interface 411 may not only be used to provide power to control center 117, but may also enable distribution of power to one or more of measurement optics 107, flow measurement device 109, pressure measurement device 111, pump 113, and/or other elements of gas sampling apparatus 100. In other embodiments, one or more of measurement optics 107, flow measurement device 109, pressure measurement device 111, pump 113, and/or other elements of gas sampling apparatus 100 may have alternate or independent power sources.

Those having skill in the art will appreciate that the invention described herein may work with various system configurations. Accordingly, more or less of the aforementioned system components may be used and/or combined in various embodiments. It should also be understood that the functionalities described herein may be implemented in various combinations of hardware and/or firmware, in addition to, or instead of, software.

In some embodiments, gas sampling apparatus 100 may include other components. For example, gas sampling apparatus 100 may include a temperature measurement device for measuring the temperature of the gas sample within gas sampling circuit 102 (contact and non-contact models are known in the art). In another example, gas sampling apparatus 100 may include a humidity measurement device for measuring the humidity or moisture present in the gas sample within the gas sampling device. Information regarding the temperature and/or humidity of the gas sample within gas sampling circuit 102 may be useful in the calculation of the infrared absorption of components within a gas sample (e.g., permits corrections to be made for the presence of water vapor) or may be used for other purposes.

In another example, gas sampling apparatus 100 may include a length of moisture permeable tubing integrated in to tubing set 103. For example, a length of Nafion™ tubing may be incorporated into tubing set 103. This moisture permeable or hydrophilic tubing may allow moisture to pass out of, or in to, the gas sample within gas sampling circuit 102 to regulate the moisture level within gas sampling circuit 102. In other embodiments, gas sampling apparatus 100 may include a water trap or other device for removing moisture or other components from gas sample prior to gas sample being analyzed in sample cell 105.

In one embodiment, one or more portions of tubing set 103 may include dual lumen tubing. Dual lumen tubing may include a length of tubing with two separate passages for carrying the gas sample. In some embodiments, dual lumen tubing may be utilized to carry a gas sample towards and away from one or more components of gas sampling apparatus 100 (e.g., sample cell 105, flow measurement device 109, pressure measurement device 111, pump 113, or other component). For example, the gas sample may be carried to sample cell 105 in a first lumen of the dual lumen tube and away from sample cell 105 in a second lumen of the dual lumen tube.

Figure 5:
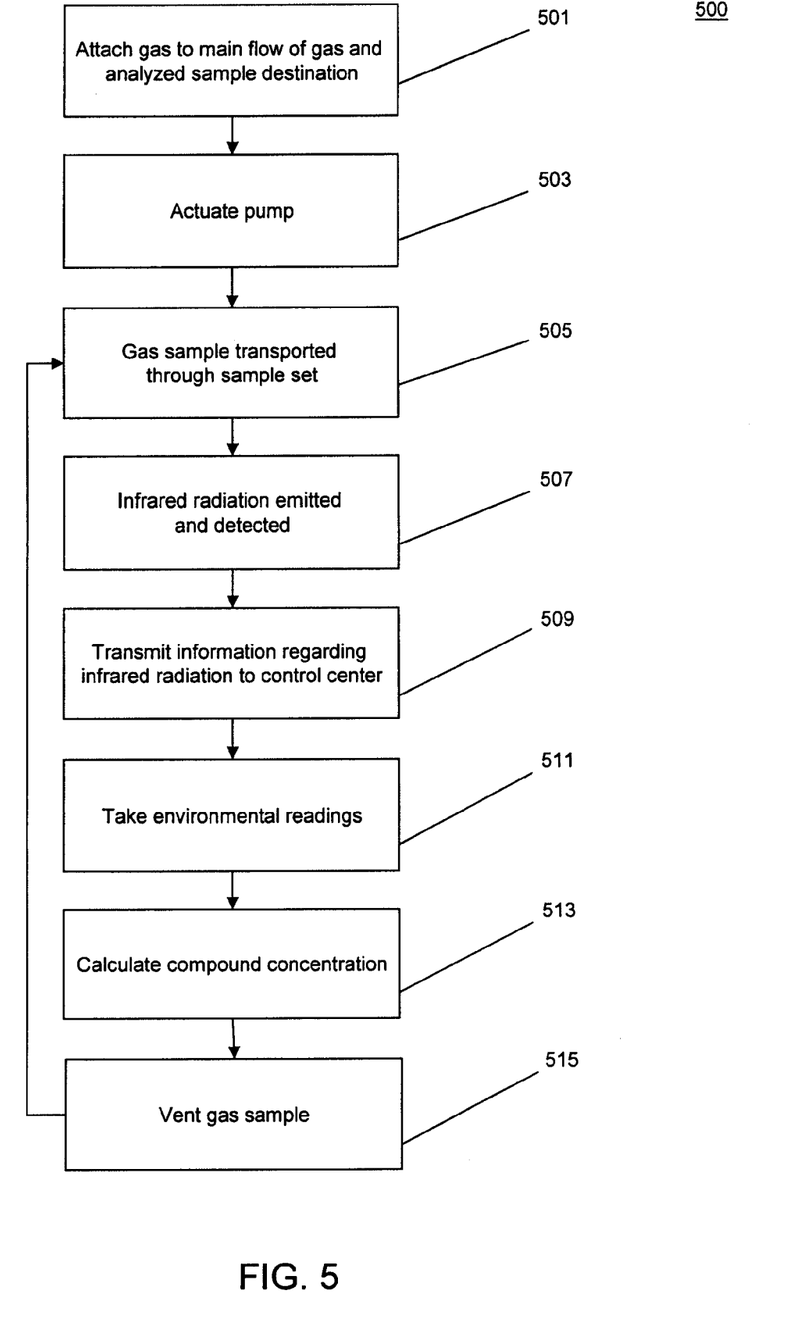
FIG. 5 is a schematic diagram of a process for analyzing a gas sample according to an embodiment of the invention.

FIG. 5 illustrates a process 500, wherein a characteristic of a component in a gas sample may be analyzed using a gas sampling apparatus having a gas sample circuit that does not interface with one or more reusable components (e.g., gas sampling apparatus 100). In one embodiment, process 500 may include an operation 501, wherein airway adaptor 101 of gas sampling apparatus 100 is attached to main flow of gas 106 and exhaust port 115 may be attached to an analyzed gas sample destination.

In an operation 503, pump 113 may be actuated to create a pressure differential that creates a sample flow of gas in gas sampling circuit 102. For example, in one embodiment, pump 113 creates a negative pressure differential that draws a gas sample from main flow of gas 106 via coupling 101, and transports the gas sample through gas sampling circuit 102. As mentioned above, in some embodiments, pump 113 does not make contact with the gas sample. Also, as mentioned above, the peristaltic pump illustrated as pump 113 is exemplary only. Pump 113 may comprise a diaphragm pump, a Venturi vacuum pump, a positive pressure displacement pump, an electroactive polymer actuated pump, or other pump.

In an operation 505, the gas sample may be transported through tubing set 103 to sample cell 105. In an operation 507, while the gas sample is in the sample analysis region of sample cell 105, infrared radiation or other radiation may be emitted from source assembly 201 of measurement optics 107. This infrared radiation may pass through the sample analysis region, including the gas sample, and be detected by detector assembly 203 of measurement optics 107, less any infrared radiation absorbed by the components of the gas sample. In other embodiments, characteristics of gas sample components may be measured using measurement techniques other than infrared absorption. For example, a measurement portion other than measurement optics 107 may be used, such as, a luminescence quenching apparatus, a solid state gas sensor, a surface acoustic wave sensor, or other measurement apparatus.

In an operation 509, the information regarding the infrared radiation detected by detector assembly 203 may be sent to control center 117. In an operation 511, one or more components of gas sampling apparatus 100 may take environmental readings regarding gas sampling circuit 102 and transmit that information to control center 117. These environmental readings may be used to account for the conditions under which the characteristics of one or more components within the gas sample are measured. For example, in one embodiment, pressure measurement device 111 may take pressure readings regarding gas sampling circuit 102. These pressure readings may be used to compensate for the effects that pressure has on the absorption of radiation by the constituents of the gas sample. Other environmental readings (e.g., flow, temperature, humidity, or other readings) may be taken and used. Operation 511 may occur while the infrared radiation is emitted and/or detected in operation 507.

In an operation 513, the measured characteristics of the concentration or other characteristic of one or more components within the gas sample may be calculated by control center 117. In some embodiments, this data may be displayed or otherwise communicated to a user.

In an operation 515, the gas sample may be vented to an analyzed gas sample destination. As mentioned above, the analyzed gas sample destination may include, for example, a scavenging system, main flow of gas 106 from which it was obtained, a disposal system, the atmosphere, or other destination. In some embodiments, process 500 may return to operation 505, wherein gas samples are continuously drawn from main flow of gas 106 and analyzed.

Gas analysis apparatus 100 may be utilized to observe real-time or near real time concentration or other characteristic of sample components in a patient's breath over a period of time. As such the "gas sample" referred to herein may represent a discrete quantity of gas that is in the analysis region of sample cell 105 at a given time. Additionally the "gas sample" may refer to the continuous flow of gas that is removed from main flow of gas 106 and analyzed for concentration or other characteristic. In some embodiments, the analysis of a continuous flow of gas over a period of time may produce a graphical display of a characteristic of one or more of the patient's breath over the period of time (e.g., a "capnogram" of $CO_2$ concentration over time).

In obtaining readings of the characteristics of one or more components of a patient's exhaled breath over a period of time, it is desirous that the flow of gas through gas sampling circuit 102 is maintained at a constant rate. Therefore, during any of the operations of process 500, flow measurement device 109 may be utilized to measure the flow of gas through gas sampling circuit and convey information regarding the flow of gas through gas sampling circuit 102 to control center 117. This information may be utilized to adjust pump 113 to maintain a constant flow of gas through gas sampling circuit 102 under different load conditions. For example, a filter incorporated into gas sampling circuit 102 may become partially clogged, thus, the load on pump 113 may increase. In another example the pressure in main flow of gas 106 from which the gas sample is drawn may increase or decrease. This may cause the load on pump 113 to increase or decrease. Other factors may alter the load on pump 113.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for measuring a concentration of one or more components of a gas sample taken from a mainstream flow of gas, the method comprising acts of: (a) providing a first assembly adapted to communicate a gas sample from a gas sampling site to a gas measuring site, the first assembly including components that contact the gas sample during use; (b) providing a second assembly that is external to the first assembly at all times during use such that all mechanical portions of the second assembly do not contact the gas sample; (c) coupling the first assembly to the second assembly; (d) carrying a gas sample from the gas sample site to the gas measuring site using a first component of the first assembly; (e) using a first component of the second assembly to perform at least one of the following functions: obtaining flow information regarding a flow of the gas sample and obtaining pressure information regarding a pressure of the gas; (f) measuring a characteristic of one or more components within the gas sample using a second component of the second assembly; and (g) integrating one or more elements into the first assembly that enables at least one of the obtaining flow information regarding the flow of the gas sample and the obtaining pressure information regarding the pressure of the gas.

2. The method of claim 1, further comprising an act of using a second component of the second assembly to move the gas sample through the first component of the first assembly.

3. The method of claim 1, further comprising acts of: decoupling the coupling of the first assembly to the second assembly after a first measuring process is complete; disposing of the first assembly; and reusing the second assembly with another first assembly in a second measuring process.

4. The method according to claim 1, further comprising at least one of the following acts, filtering the gas sample using the first assembly or dehumidifying the gas sample using the first assembly.

5. A sidestream gas sampling apparatus, comprising: (a) a gas sampling circuit comprising: (1) a sample transport tube that receives a gas sample from a mainstream flow of gas, wherein a portion of the sample transport tube is modified to include a sample analyzer region in which a characteristic of one or more components within the gas sample is measured without any mechanical portions of measuring devices contacting the gas sample; and (b) a pump that creates a pressure differential within the gas sampling circuit to remove the gas sample from the mainstream flow of gas and move the gas sample through the sample transport tube to the sample analyzer region wherein the pump does not make contact with the gas sample, wherein the sample transport tube includes one or more elements integrated into the transport tube that permit the measurement of the characteristic of one or more components within the gas sample without any mechanical portions of the measuring devices contacting the gas sample.

6. The apparatus of claim 5, wherein at least one of the sample transport tube or the sample analyzer region includes at least one of a solid-state gas sensor or a surface acoustic wave (SAW) sensor.

7. The apparatus of claim 5, wherein the characteristic of the one or more components within the gas sample comprises: (a) one or more of a concentration of the one or more components within the gas sample and a partial pressure of the one or more components within the gas sample comprises the concentration; or (b) one or more components within the gas sample expressed as one or more of a percentage, parts per million (ppm), and parts per billion (ppb).

8. The apparatus of claim 5, wherein the measuring devices measure characteristics of the one or more components within the gas sample using one or more devices structured to perform spectroscopy, infrared spectroscopy, or luminescence quenching.

9. The apparatus of claim 5, wherein the integrated component of the sample analyzer region comprises at least one of the following at least two optical analysis windows integrated into the sample transport tube, and one or more electrical contacts that permit physical communication with a solid-state gas sensor or a surface acoustic wave sensor.

10. The apparatus of claim 5, wherein the sample analyzer region comprises at least two optical analysis windows integrated into the sample transport tube.

11. The apparatus of claim 5, wherein the one or more components whose characteristic within the gas sample is measured is one or more of carbon dioxide (CO2), carbon monoxide (CO), oxygen (O2), nitric oxide (NO), and anesthetic agents.

12. The apparatus of claim 5, wherein the pump comprises one or more of a diaphragm pump, a peristaltic pump, a Venturi vacuum pump, and an electroactive polymer actuated pump.

13. The apparatus of claim 5, wherein the sample transport tube comprises first and second lumens, wherein the first lumen carries the gas sample towards the sample analyzer region, and wherein the second lumen carries the gas sample away from the sample analyzer region.

14. The apparatus of claim 5, further comprising an adapter that removes the gas sample from the mainstream flow of gas and introduces the gas sample into the gas sampling circuit.

15. The apparatus of claim 5, wherein the gas sampling circuit further comprises a sample exhaust port that expels the gas sample from the gas sampling circuit after it has passed through the sample analyzer region.

16. The apparatus of claim 15, wherein the sample exhaust port is structured to perform at least one of the following: (a) returning the gas sample to the mainstream flow of gas, or (b) transporting the gas sample to a disposal apparatus.

17. The apparatus of claim 5, wherein the sample transport tube includes a moisture removal region that removes moisture from the gas sample.

18. The apparatus of claim 17, wherein the moisture removal region comprises at least one of the following: a section of hydrophilic tubing, a dehumidifying material, or a water trap.

19. The apparatus of claim 5, wherein the measuring devices comprise at least one of the following (a) a flow measurement device that obtains information regarding a flow rate of the gas sample through the gas sampling circuit and (b) a pressure measurement device that obtains information regarding a pressure of the gas sample within the gas sampling circuit.

20. The apparatus of claim 19, wherein:
at least one of the sample transport tube or the sample analyzer region includes a sensing element for a vortex shedding flowmeter;
wherein the measuring device comprises a flow measurement device and wherein the flow measurement device includes a vortex shedding flowmeter; and
the sensing element is structured to be operatively coupled to the vortex shedding flowmeter.

21. The apparatus of claim 19, wherein the measuring devices comprise a flow measurement device, and wherein information regarding the flow of the gas sample through the gas sampling circuit is utilized to control the pump to ensure a constant flow of gas through the gas sampling circuit.

22. The apparatus of claim 19, wherein the measuring devices comprise a flow measurement device, and wherein the flow measurement device comprises one of an optical flowmeter, an ultrasonic flowmeter, or a thermal mass flowmeter.

23. The apparatus of claim 19, wherein the measuring devices comprise a pressure measurement device, and wherein:
the sample integrated component of the transport tube includes an integrated is a diaphragm; and
the pressure measurement device measures the deformity of the diaphragm to measure the pressure within the gas sampling circuit.

24. The apparatus of claim 19, wherein the measuring devices comprise a pressure measurement device, and wherein the information regarding the pressure of the gas sample within the gas sampling circuit is utilized to account for effects the pressure has on the measurement of the characteristic of the one or more components within the gas sample.

25. A method for measuring a concentration of one or more components of a gas sample taken from a mainstream flow of gas, the method comprising acts of: removing a gas sample from a mainstream flow of gas; transporting the gas sample to a sample analyzer region via a sample transport tube; measuring a characteristic of the one or more components within the gas sample in the sample analyzer region using a detector assembly; integrating one or more elements into the sample analyzer region that enables the measuring of the characteristics of the one or more components within the gas sample, wherein all mechanical portions of the detector assembly do not contact the gas sample; and pumping the gas sample through the sample transport tube using a pump mechanism that does not contact the gas sample.

26. The method according to claim 25, wherein the pumping the gas sample is performed by a pump, and wherein the pump operatively engages the transport tube and wherein the method further comprising an act of replacing the sample transport tube for use with the same pump mechanism.

27. The method according to claim 25, further comprising at least one of the following acts, (a) obtaining flow information regarding a flow of the gas sample without making contact with the gas sample, or (b) obtaining pressure information regarding a pressure of the gas sample without making contact with the gas sample.

28. A sidestream gas sampling system, comprising:
a first assembly adapted to communicate a gas sample from a gas sampling site to a gas measuring site, the first assembly including components that contact the gas sample during use, wherein the first assembly includes: (1) a sample transport tube that receives a gas sample from the gas sample site, and (2) a sample analyzer region in which a characteristic of one or more components within the gas sample is measured; and
a second assembly that is external to the first assembly at all times during use such that all mechanical portions of the second assembly do not contact the gas sample, wherein the second assembly includes at least one of a flow measurement device that obtains information regarding a flow of the gas sample through the sample transport tube and a pressure measurement device that obtains information regarding a pressure of the gas sample within the sample transport tube, wherein the sample analyzer region includes one or more elements integrated into the transport tube that permit at least one of the flow measurement device to obtain the information regarding the flow of the gas sample and the pressure measurement device to obtain the information regarding the pressure of the gas sample.

29. The system of claim 28, wherein:
said first assembly includes a sensing element for a vortex shedding flowmeter;
the second assembly includes the flow measurement device including a vortex shedding flowmeter; and
the sensing element is structured to be operatively coupled to the vortex shedding flowmeter.

30. The system of claim 28, wherein the sample transport tube includes at least one prong adapted to communicate with an airway of a patient.

31. The system of claim 28, wherein the sample transport tube and the sample analyzer region are defined as a unitary component.

32. The system of claim 28, wherein the first assembly further includes elements selected from the group comprising: (a) an adapter adapted to couple the sample transport tube to a patient circuit; (b) a filter operatively coupled to at least one of the sample transport tube or the sample analyzer region; and (c) a moisture removal system operatively coupled to at least one of the sample transport tube or the sample analyzer region, wherein the moisture removal system is adapted to remove moisture from the gas sample.

33. The system of claim 28, wherein the second assembly includes the flow measurement device and the flow measurement device comprises one of an optical flowmeter, an ultrasonic flowmeter, or a thermal mass flowmeter.

34. The system of claim 28, wherein the second assemble includes a pump operatively coupled to the sample transport tube and structured to move the gas sample through the sample transport tube to the sample analyzer region and the pump comprises one or more of a diaphragm pump, a peristaltic pump, a Venturi vacuum pump, and an electroactive polymer actuated pump.

35. The system of claim 28, wherein the integrated component of the sample analyzer region includes at least one of the following: at least two optical analysis windows integrated into the sample transport tube and one or more electrical contacts that permit physical communication with a solid-state gas sensor or a surface acoustic wave sensor.

* * * * *